US012570689B2

(12) United States Patent
Patil et al.

(10) Patent No.: US 12,570,689 B2
(45) Date of Patent: Mar. 10, 2026

(54) PURIFICATION OF GLP-1 ANALOGUES

(71) Applicant: BIOCON LIMITED, Bangalore (IN)

(72) Inventors: Nitin Sopanrao Patil, Bangalore (IN);
Ramachandran Ganesh, Bangalore
(IN); Onkar Prakash Santan,
Bangalore (IN); Abhijeet Arun Lambe,
Kolhapur (IN); **Kruthi Sathish
Bastikoppa**, Karnataka (IN);
Kathiravan Sindhuamuthan,
Virudhunagar (IN)

(73) Assignee: BIOCON LIMITED, Bangalore (IN)

(*) Notice: Subject to any disclaimer, the term of this
patent is extended or adjusted under 35
U.S.C. 154(b) by 782 days.

(21) Appl. No.: 17/428,776

(22) PCT Filed: Feb. 5, 2020

(86) PCT No.: PCT/IB2020/050915
§ 371 (c)(1),
(2) Date: Aug. 5, 2021

(87) PCT Pub. No.: WO2020/161636
PCT Pub. Date: Aug. 13, 2020

(65) Prior Publication Data
US 2022/0411464 A1 Dec. 29, 2022

(30) Foreign Application Priority Data
Feb. 6, 2019 (IN) .............................. 201941004693

(51) Int. Cl.
| | |
|---|---|
| *C07K 1/16* | (2006.01) |
| *A61K 38/26* | (2006.01) |
| *A61P 3/04* | (2006.01) |
| *A61P 3/10* | (2006.01) |
| *C07K 14/605* | (2006.01) |

(52) U.S. Cl.
CPC ................ *C07K 1/16* (2013.01); *A61K 38/26*
(2013.01); *A61P 3/04* (2018.01); *A61P 3/10*
(2018.01); *C07K 14/605* (2013.01)

(58) Field of Classification Search
CPC .... C07K 1/16; C07K 14/605; C07K 14/7051;
A61K 38/26; A61P 3/04; A61P 3/10
See application file for complete search history.

(56) References Cited

U.S. PATENT DOCUMENTS

| | | | | |
|---|---|---|---|---|
| 7,125,492 B2 * | 10/2006 | Bidlingmeyer | ...... | B01D 15/325 |
| | | | | 210/656 |
| 2010/0183876 A1 * | 7/2010 | Hell | ......................... | A61K 9/14 |
| | | | | 530/308 |
| 2015/0051372 A1 * | 2/2015 | Qin | ......................... | C07K 1/16 |
| | | | | 530/308 |

FOREIGN PATENT DOCUMENTS

| | | | | |
|---|---|---|---|---|
| WO | 2013117135 A1 | 8/2013 | | |
| WO | 2016059609 A1 | 4/2016 | | |
| WO | WO-2016067271 A1 * | 5/2016 | ........... | C07K 14/605 |
| WO | 2018104922 A1 | 6/2018 | | |
| WO | 2020161636 A1 | 8/2020 | | |

OTHER PUBLICATIONS

Baheti, KG; et al. "Ion-pairing reverse-phase high performance liquid chromatography method for simultaneous estimation of atenolol and indapamide in bulk and combined dosage form", May-Jun. 2012, Indian Journal of Pharmaceutical Sciences, p. 271-274. (Year: 2012).*

David Gétaz, et al. "Modeling of ion-pairing effect in peptide reversed-phase chromatography", Journal of Chromatography A, vol. 1249, 2012, pp. 92-102, ISSN 0021-9673, https://doi.org/10.1016/j.chroma.2012.06.005. (Year: 2012).*

Dacheng Guo, et al. Effects of ion-pairing reagents on the prediction of peptide retention in reversed-phase high-resolution liquid chromatography, Journal of Chromatography A, vol. 386, 1987, pp. 205-222, ISSN 0021-9673, https://doi.org/10.1016/S0021-9673(01)94598-4.), (Year: 1987).*

Richard I. Senderoff, et al. "Consideration of Conformational Transitions And Racemization During Process Development of Recombinant Glucagon-Like Peptide-1", Journal of Pharmaceutical Sciences, vol. 87, Issue 2, 1998, pp. 183-189, ISSN 0022-3549, https://doi.org/10.1021/js9702729. (Year: 1998).*

Shimadzu et al., "Ion Pair Chromatography-Differentiating When to Use Alkyl Sulfonates and Perchlorates", available online at: www.shimadzu.com/an/hplc/support/lib/lctalk/27/27lab.html, available on the internet from Jul. 10, 2013 (Year: 2013).*

Senderoff RI, Kontor KM, Kreilgaard L, Chang JJ, Patel S, Krakover J, Heffernan JK, Snell LB, Rosenberg GB. Consideration of conformational transitions and racemization during process development of recombinant glucagon-like peptide-1. Journal of pharmaceutical sciences. Feb. 1, 1998;87(2):183-9. (Year: 1998).*

Getaz D, Hariharan SB, Butte A, Morbidelli M. Modeling of ion-pairing effect in peptide reversed-phase chromatography. Journal of Chromatography A. Aug. 3, 2012;1249:92-102. (Year: 2012).*

Ion Pair Chromatography—Differentiating When to Use Alkyl Sulfonates and Perchlorates (https://www.shimadzu.com/an/hplc/support/lib/lctalk/27/27lab.html, available on the internet from Jul. 10, 2013).

(Continued)

Primary Examiner — Jennifer M.H. Tichy
Assistant Examiner — Emily F Eix
(74) Attorney, Agent, or Firm — KATTEN MUCHIN ROSENMAN LLP

(57) ABSTRACT

The present invention provides for purification of liraglutide using selective ion-pairing agents in the reversed phase-high performance liquid Chromatography, for purifying crude liraglutide from closely related impurities.

9 Claims, 4 Drawing Sheets

(56) References Cited

OTHER PUBLICATIONS

Knudsen, Lotte B., "Potent Derivatives of Glucagon-like Peptide-1 with Pharmacokinetic Properties Suitable for Once Daily Administration", J. Med. Chem. 2000, 43,1664-1669.

* cited by examiner

PURIFICATION OF GLP-1 ANALOGUES

CROSS-REFERENCE TO RELATED APPLICATION

This application is a U.S. National Stage Entry Application of International Application No. PCT/IB2020/050915 filed Feb. 5, 2020, which claims the benefit of priority of Indian Patent Application No. 201941004693 filed on Feb. 6, 2019, each of which is herein incorporated by reference in its entirety for all purposes.

TECHNICAL FIELD

The present invention relates to a method for purifying crude GLP-1 analogue, Liraglutide in particular which is represented by the Formula-I.

Formula -I

BACKGROUND AND PRIOR ART OF THE DISCLOSURE

Liraglutide (VICTOZA®) is a glucagon-like peptide-1 (GLP-1) receptor agonist indicated as an adjunct to diet and exercise to improve glycemic control in adults with type 2 diabetes mellitus.

Liraglutide, is a long acting analogue of the naturally occurring human glucagon like peptide-1 (GLP-1(7-37)) in which lysine at position 34 has been replaced with arginine and palmitoyl group has been attached via glutamoyl spacer to lysine at position 26.

Liraglutide (VICTOZA®), developed by Novo Nordisk got initial approval in United States in 2010 as subcutaneous injection.

Liraglutide due to its long peptide chain and high hydrophobicity due to palmitoyl group is highly difficult to purify.

Several attempts for purification of GLP-1 analogues including Liraglutide have been reported in the past.

Journal of Medicinal Chemistry 43, 1664-1669, 2000 discloses a purification process of Liraglutide by reversed phase-high performance liquid Chromatography (RP HPLC) using a cyanopropyl column (Zorbax 300SB-CN) and a standard acetonitrile/TFA system.

The method as disclosed above results in a reduced purification yield of 35%.

WO2013117135 discloses a purification process of Liraglutide by RP HPLC using Isopropyl alcohol/TFA system.

The method as disclosed involves multiple purification steps involving 3 RP HPLC operations, which is a laborious process.

GLP-1 peptides are produced either by synthetic or by recombinant approach often have closely related impurities that are difficult to separate on RP-HPLC. These impurities are either isomeric or deletion/addition based impurities that have similar characteristics like the parent molecule. These closely related impurities pose a challenge in purification.

It is well-known that the use of RP-HPLC is limited for the separation and identification of complex mixtures having components with large variation in pKa values. Thus resolution of closely eluting impurities has always been challenging in chromatographic purification.

In the resolution of organic ions with conventional HPLC methods, use of ion pair reagents can enhance peak shape and retention time when common remedies such as modifying eluent ratios or changing stationary phase fail. This technique is sometimes referred as Ion pair chromatography (IPC).

IPC is a type of RP-HPLC in which ion pair reagents are added to the mobile phase to promote the formation of ion pairs with charged analytes, which makes the reversed phase column suitable for the separation of ionic molecules. The retention/separation follows a dynamic combination of reversed phase and ion pair-ion exchange mechanisms.

Ion pair reagents are comprised of a long linear alkyl chain (from C3 up to C16) and an ionic group which can reversibly adsorb to the alkyl chains (C8 or C18) of the RP-phase, forming a dynamic ion-exchanger, at which ionic compounds can be separated. There are two main types of ion pair reagents, anionic alkyl sulfonates for basic compounds and cationic quaternary amines for acidic compounds. Commonly used Alkyl sulfonates in IPC are 1-hexanesulfonic acid sodium salt, 1-heptasulfonic acid sodium salt, 1-octanesulfonic acid sodium salt and the like. The selectivity of the system strongly depends on the choice and amount of the ion pair former in the mobile phase. Reagents with long chain lengths will considerably be better adsorbed onto the RP phase, affecting the retention in a positive way.

Separation of liraglutide from these closely related impurities was studied on RP-HPLC in absence and presence of ion pairing agents viz. sodium salts of 1-octane sulfonic acid, hexane sulfonic acid. It was observed that the resolution of closely related impurities was more effective in presence of the ion-pairing agent resulting in overall better purity as compared to the purification run, wherein ion-pairing agent was not used.

The present invention provides a method for purification of liraglutide from these closely related impurities was studied on RP-HPLC in absence and presence of ion pairing agents viz. sodium salts of propane sulfonic acid, butane sulfonic acid, pentane sulfonic acid, hexane sulfonic acid, heptane sulfonic acid, octane sulfonic acid, nonane sulfonic acid, decane sulfonic acid, undecane sulfonic acid, dodecane sulfonic acid, tridecane sulfonic acid.

It was observed that the resolution of closely related impurities was more effective in presence of the ion-pairing agent resulting in overall better purity as compared to the RP HPLC purification, wherein ion-pairing agent was not used.

SUMMARY OF THE INVENTION

Aspects of the present application provides processes for purification of liraglutide.

One aspect of the present invention discloses a method for purifying crude liraglutide, the method comprising:
- a. obtaining a solution of liraglutide by dissolving crude liragluide in a mixture comprising an aqueous acid solution and acetonitrile;
- b. subjecting the solution of crude liraglutide to a first HPLC purification using an aqueous acid solution and an ion pairing agent as mobile phase A and acetonitrile containing an alcohol as mobile phase B;
- c. Subjecting the liraglutide from first HPLC purification to a second HPLC purification; and
- d. Isolating the purified liraglutide.

Another aspect of the present invention discloses a method for purifying crude liraglutide, wherein ion-pairing agent is selected from salt of an alkane sulfonic acid.

Another aspect of the present invention discloses a method for purifying crude liraglutide, wherein the salt of an alkane sulfonic acid is selected from the group consisting of 1-octane sulfonic acid sodium salt or 1-heptane sulfonic acid sodium salt.

Another aspect of the present invention discloses a method for purifying crude liraglutide, wherein the salt of an alkane sulfonic acid is 1-hexane sulfonic acid sodium salt.

Another aspect of the present invention discloses a method for purifying crude liraglutide, wherein the aqueous acid solution is selected citric acid, acetic acid, trifluoroacetic acid or formic acid.

Another aspect of the present invention discloses a method for purifying crude liraglutide, by HPLC using ion pairing agent.

Instrumental Parameters:

HPLC Instrument Parameters:

Column: C8, 150×4.6 mm, 2.7 μm

Column temperature: 60° C.

Detection: UV

Wavelength: 215 nm

Advantages of Present Invention:

Crude liraglutide powder (Assay 20-25%; Purity 30-50%) is subjected to two sequential RP-HPLC purification steps under diverse conditions, followed by lyophilization to yield the pure Liraglutide. The present invention involves using selective ion-pairing agents in one of the RP-HPLC steps, for purifying crude liraglutide from closely related impurities.

Absence of ion pairing agents in the process, results in no or poor resolution of the related impurities, leading to the impurities in the final API.

Comparison of Liraglutide Purity Profile without & with Octane-1-Sulfonic Acid as Ion Paring Agent:

The below table provides a comparison of Liraglutide purity profile with respect to closely associated impurities present at RRT's 0.93, 0.98 & 1.06 without & with usage of Octane-1-sulfonic acid as ion paring agent.

| STAGE | Ion Paring agent | AREA (%) | | | |
| --- | --- | --- | --- | --- | --- |
| | | 0.93 RRT | 0.98 RRT | LIRA-GLUTIDE | 1.06 RRT |
| RP-HPLC-1 PURIFICATION | No Ion paring agent | 0.84 | 0.31 | 92.55 | 0.4 |
| | Octane-1-sulfonic acid sodium salt (OSA) | 0.02 | 0.08 | 94.64 | 0 |

BRIEF DESCRIPTION OF THE FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein.

DETAILED DESCRIPTION OF THE INVENTION

The embodiments of the present invention are further described using specific examples herein after. The examples are provided for better understanding of certain embodiments of the invention and not, in any manner, to limit the scope thereof. Possible modifications and equivalents apparent to those skilled in the art using the teachings of the present description and the general art in the field of the invention shall also form the part of this specification and are intended to be included within the scope of it.

EXAMPLES

Example 1

275.5 mg of crude Liraglutide, obtained from solid-phase synthesis was dissolved in 250 mM Citric acid monohydrate containing 10% Acetonitrile (v/v) filtered and subjected to a two-step RP-HPLC purification.

RP-HPLC-1:

The crude liraglutide solution was loaded onto a 20 ml of C8-substituted silica column (particle size 10-13 μm) equilibrated with about 60 ml of 100 mM citric acid containing 0.05% w/v octane-1-sulphonic acid sodium salt (Mobile Phase A), 25% Acetonitrile:Isopropanol (7:3) (Mobile Phase B) pH 2.0. Post loading the column was washed with 8:2 Buffer A:Buffer B. Product was eluted by applying a gradient upto 60% B. Detection wavelength was kept at 215 nm. The chromatographic temperature was kept at 25° C. Fractions with purity of >91% were pooled and the average pool purity at RP-1 was >95% with closely related impurities less than 0.50%.

The liraglutide product from RP-HPLC-1 was taken further for RP-HLC-2.

Example 2

275.5 mg of crude Liraglutide, obtained from solid-phase synthesis was dissolved in 250 mM Citric acid monohydrate containing 10% Acetonitrile (v/v) filtered and subjected to a two-step RP-HPLC purification.

RP-HPLC-1:

The crude liraglutide solution was loaded onto a 20 ml of C8-substituted silica column (particle size 10-13 μm) equilibrated with about 60 ml of 100 mM citric acid containing 0.05% 1-hexane sulphonic acid sodium salt (Mobile Phase A), 25% Acetonitrile:Isopropanol (7:3) (Mobile Phase B) pH 2.0. Post loading the column was washed with 8:2 Buffer A:Buffer B. Product was eluted by applying a gradient upto 60%. Detection wavelength was kept at 215 nm. The chromatographic temperature was kept at 25° C. Fractions were collected and analyzed for purity. Fractions with purity of >91% were pooled.

Figure 4:
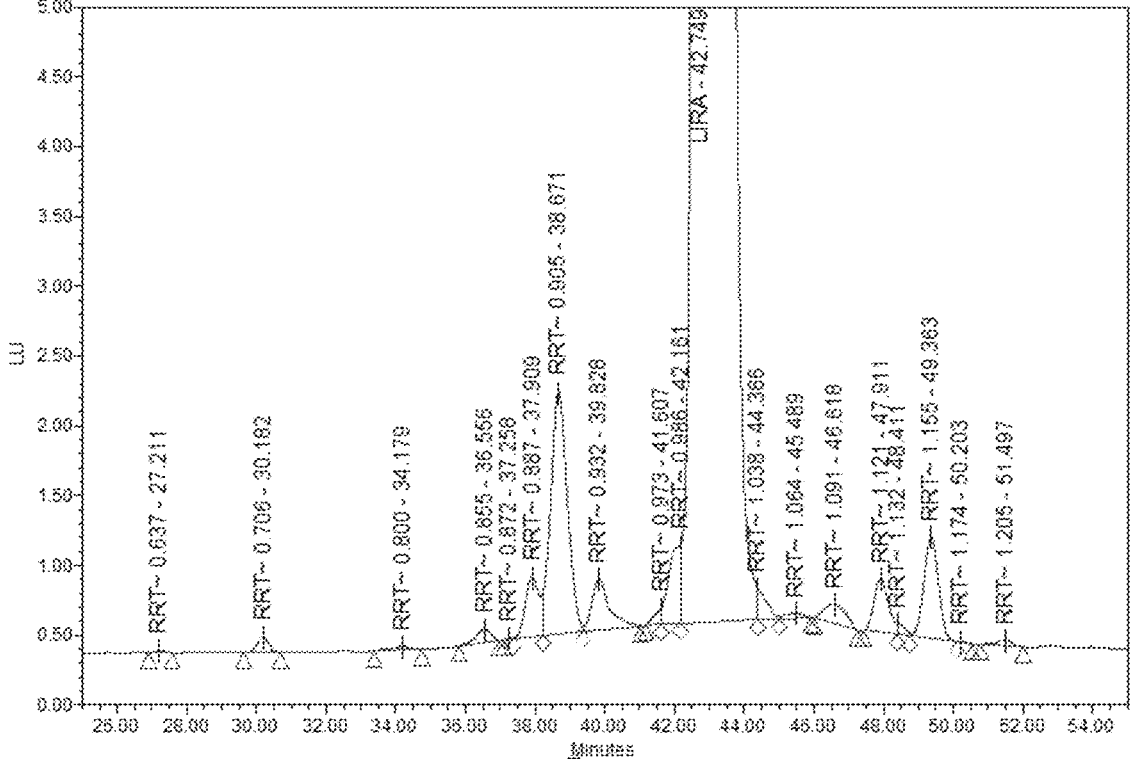
FIG. 4: Illustrates the HPLC pattern of Liraglutide of Formula I after purification with usage of HSA.

The purity of the RP-HPLC-1 purified liraglutide HPLC chromatogram is as shown in FIG. 4.

HPLC purity of the RP-HPLC-1 purified liraglutide was >95% with closely related impurities less than 2.0% pH of these pool was adjusted to 7.8 and distilled at 35° C. to remove organic solvent. Precipitation was done at pH-4.9 and RP-HPLC-1 purified liraglutide was isolated.

The liraglutide product from RP-HPLC-1 was taken further for RP-HLC-2.

Example 3

275.5 mg of crude Liraglutide, obtained from solid-phase synthesis was dissolved in 250 mM Citric acid monohydrate containing 10% Acetonitrile (v/v) filtered and subjected to a two-step RP-HPLC purification.

RP-HPLC-1:

The crude liraglutide solution was loaded onto a 20 ml of C8-substituted silica column (particle size 10-13 μm) equilibrated with about 60 ml of 100 mM citric acid (Mobile Phase A), 25% Acetonitrile:Isopropanol (7:3) (Mobile Phase B) pH 2.0. Post loading the column was washed with (8:2) Buffer A:Buffer B. Product was eluted by applying a gradient upto 60% B. Detection wavelength was kept at 215 nm. The chromatographic temperature was kept at 25° C. Fractions were collected and analyzed for purity. Fractions with purity of >91% were pooled.

HPLC purity of the RP-HPLC-1 purified liraglutide was >95% with closely related impurities less than 2.0%.

Figure 1:
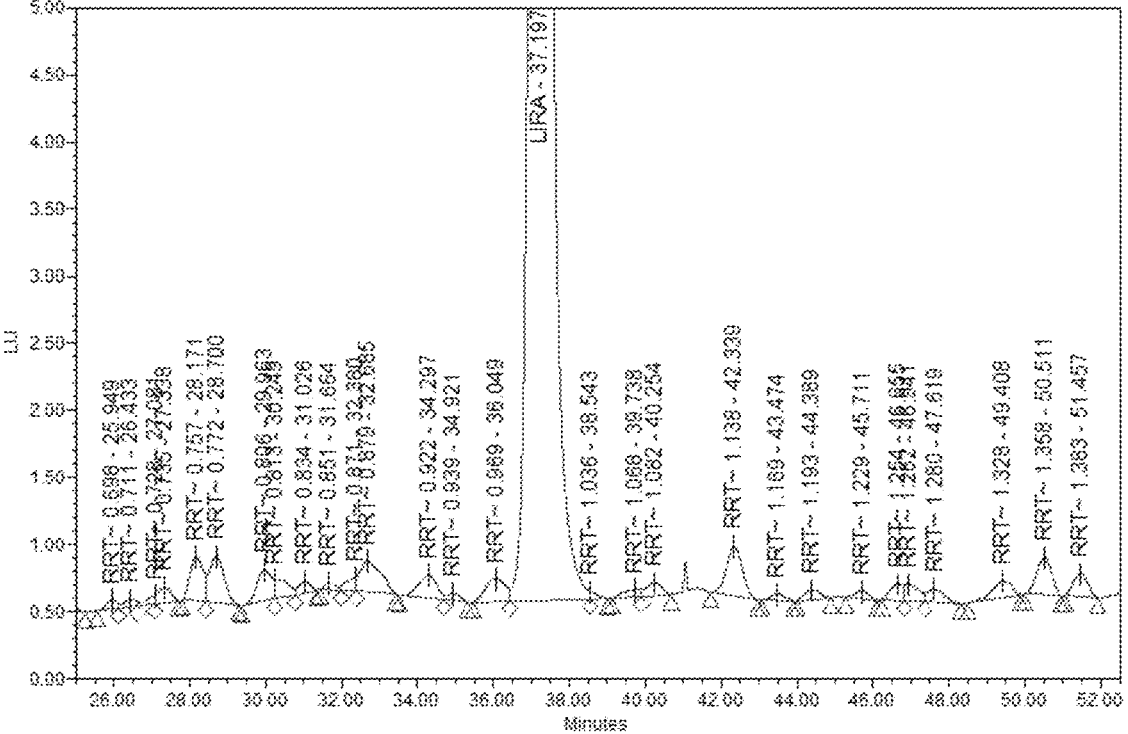
FIG. 1: Illustrates the HPLC pattern of crude Liraglutide of Formula I.
Figure 2:
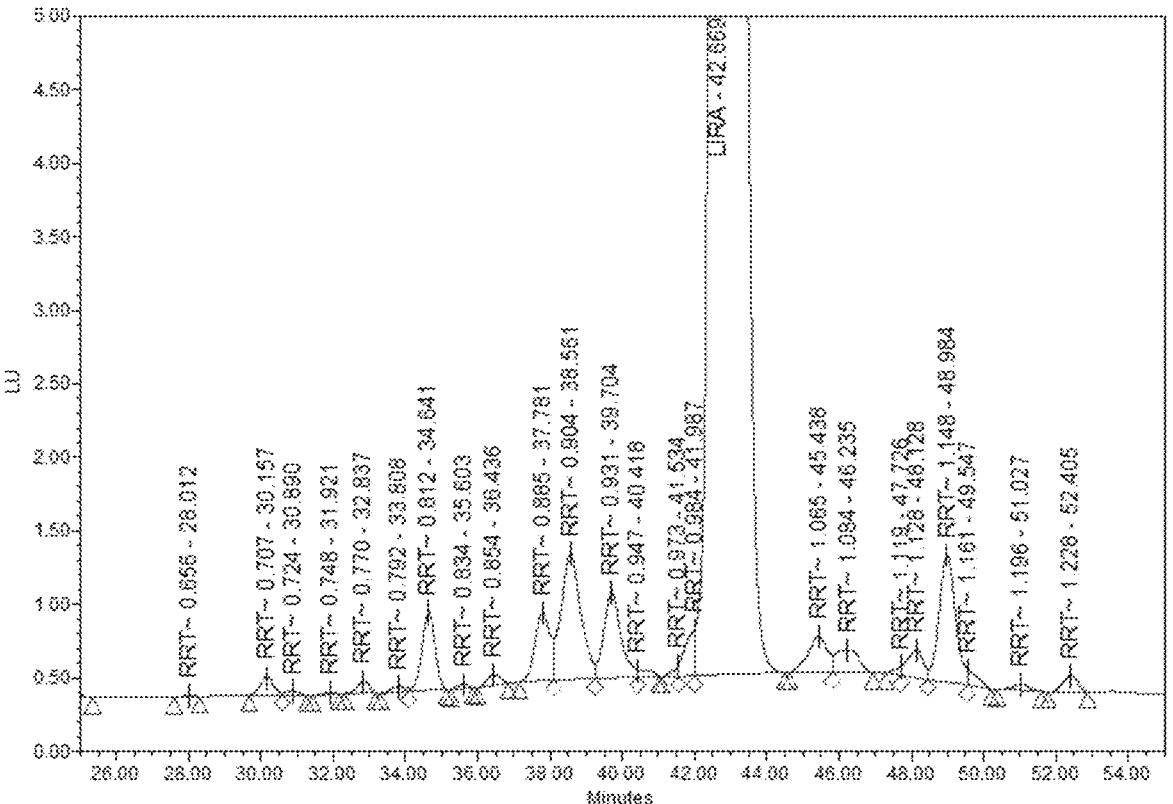
FIG. 2: Illustrates the HPLC pattern of Liraglutide of Formula I after purification without usage of OSA.

The purity of the RP-HPLC-1 purified liraglutide HPLC chromatogram is as shown in FIG. 2.

The liraglutide product from RP-HPLC-1 was taken further for RP-HLC-2.

Example 4

32.6 g of crude Liraglutide, obtained from solid-phase synthesis was dissolved in 250 mM Citric acid monohydrate containing 10% Acetonitrile (v/v) filtered and subjected to a two-step RP-HPLC purification.

Figure 3:
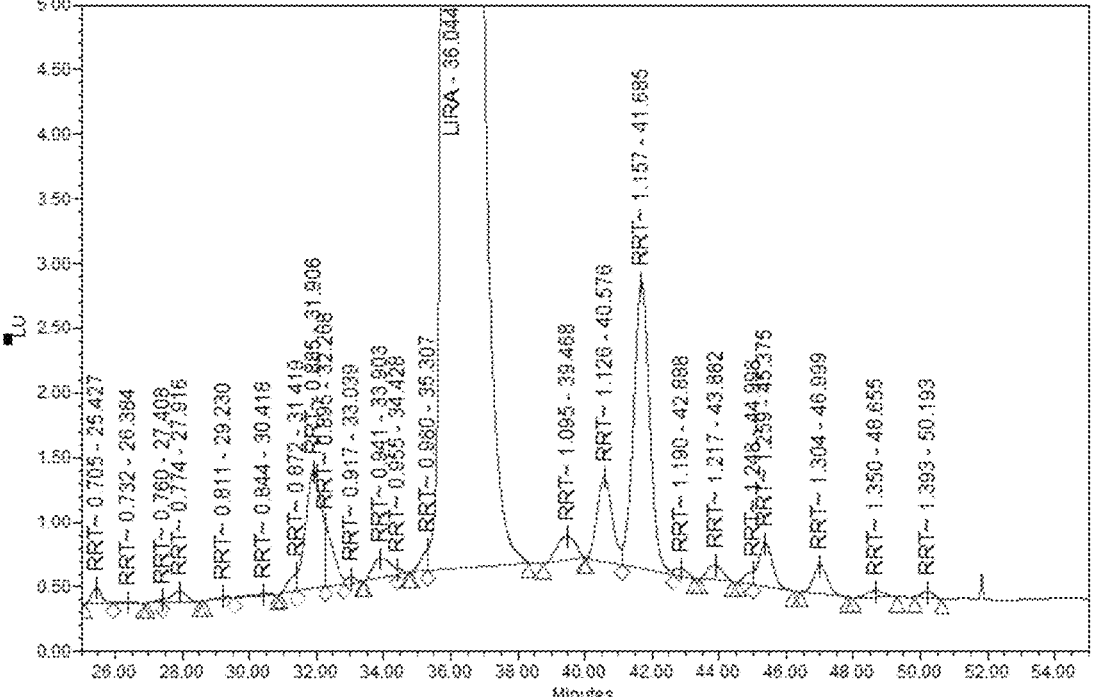
FIG. 3: Illustrates the HPLC pattern of Liraglutide of Formula I after purification with usage of OSA.

RP-HPLC-1:

The crude liraglutide solution was loaded onto a 2.4 L of C8-substituted silica column (particle size 10-13 μm) equilibrated with about 7.2 L of 100 mM citric acid containing 0.05% octane-1-sulphonic acid sodium salt (Mobile Phase A), 25% Acetonitrile:Isopropanol (7:3) (Mobile Phase B) pH 2.0. Post loading the column was washed with 8:2 Buffer A:Buffer B. Product was eluted by applying a gradient upto 60% B. Detection wavelength was kept at 215 nm. The chromatographic temperature was kept at 25° C. Fractions were collected and analyzed for purity. Fractions with purity of >91% were pooled. The purity of the RP-HPLC-1 purified liraglutide HPLC chromatogram is as shown in FIG. 3.

HPLC purity of the RP-HPLC-1 purified liraglutide was >94% with closely related impurities less than 0.50%.

pH of these pool was adjusted to 7.8 and distilled at 35° C. to remove organic solvent. Precipitation was done at pH-4.9 and RP-HPLC-1 purified liraglutide was isolated.

The liraglutide product from RP-HPLC-1 was taken further for RP-HLC-2.

RP-HPLC-2:

3.1 L of the RP-HPLC-1 purified liraglutide dissolved in 50 mM Di-Sodium hydrogen phosphate containing 25% Methanol at 3 mg/ml was loaded onto a 2.4 L of C8-substituted silica column (particle size 10-13 μm) equilibrated with about 7.2 L of 50 mM Sodium phosphate buffer pH 7.5 containing 5% Acetonitrile. Product was eluted by applying a gradient upto 41% B. Detection wavelength was kept at 215 nm. The chromatographic temperature was kept at 25° C. Individual fractions were collected and analyzed for purity. Fractions with purity of >98.0% were pooled and distilled at 35° C. to remove organic solvent. Precipitation was done at pH 4.9. The purified Liraglutide was subjected to lyophilization. HPLC purity of the lyophilized powder was >99% with no impurity more than 0.20%.

The invention claimed is:

1. A method for purifying crude liraglutide, the method consisting of:
   a. obtaining a solution of liraglutide by dissolving crude liragluide in a mixture of an aqueous acid solution and acetonitrile;
   b. subjecting the solution of liraglutide to a first high pressure liquid chromatography purification using an aqueous acid solution and an ion pairing agent as mobile phase A and acetonitrile containing an alcohol as mobile phase B;
   c. subjecting the liraglutide obtained from first high pressure liquid chromatography purification in step b. to a second high pressure liquid chromatography purification; and
   d. isolating the purified liraglutide obtained from the second high pressure liquid chromatography purification in step c, wherein the purified liraglutide has HPLC purity of >99%, and
   wherein, the ion pairing agent is a salt of an alkane sulfonic acid.

2. The method of claim 1, wherein the salt of an alkane sulfonic acid is selected from the group consisting of 1-octane sulfonic acid sodium salt, 1-hepta sulfonic acid sodium salt and 1-hexane sulfonic acid sodium salt.

3. The method of claim 1, wherein the salt of an alkane sulfonic acid is 1-octane sulfonic acid sodium salt.

4. The method of claim 1, wherein the aqueous acid solution used in step (a) is selected from citric acid, acetic acid, trifluoroacetic acid and formic acid.

5. The method of claim 1, wherein the alcohol is isopropanol.

6. The method of claim 1, wherein the concentration of the alcohol in the acetonitrile is about 70%.

7. The method of claim 1, wherein the liraglutide obtained in step b is a solid.

8. The method of claim 1, wherein the liraglutide obtained in step c is a solid.

9. The method of claim 1, wherein the purified liraglutide has HPLC purity of >99% with no impurity more than 0.2%.

\* \* \* \* \*